(12) United States Patent
Fatahi

(10) Patent No.: US 11,649,415 B2
(45) Date of Patent: May 16, 2023

(54) OIL-WATER COMPOSITIONS, METHODS, AND USES THEREOF

(71) Applicant: Reza Fatahi, Encino, CA (US)

(72) Inventor: Reza Fatahi, Encino, CA (US)

(*) Notice: Subject to any disclaimer, the term of this patent is extended or adjusted under 35 U.S.C. 154(b) by 0 days.

(21) Appl. No.: 17/177,205

(22) Filed: Feb. 17, 2021

(65) Prior Publication Data

US 2021/0179968 A1 Jun. 17, 2021

Related U.S. Application Data

(63) Continuation-in-part of application No. 16/724,296, filed on Dec. 22, 2019, now abandoned, and a continuation-in-part of application No. 16/389,935, filed on Apr. 20, 2019, now abandoned, and a continuation-in-part of application No. 16/294,852, filed on Mar. 6, 2019, now abandoned, and a continuation-in-part of application No. 16/270,606, filed on Feb. 8, 2019, now abandoned.

(51) Int. Cl.

| | |
|---|---|
| *C11B 9/00* | (2006.01) |
| *A61K 47/44* | (2017.01) |
| *A61K 31/59* | (2006.01) |
| *A61K 47/10* | (2017.01) |
| *A01N 65/06* | (2009.01) |
| *A01N 65/40* | (2009.01) |
| *C11D 3/50* | (2006.01) |
| *C11D 3/382* | (2006.01) |
| *C11D 1/66* | (2006.01) |
| *A61K 9/00* | (2006.01) |
| *A01N 25/04* | (2006.01) |
| *A61K 9/107* | (2006.01) |

(52) U.S. Cl.
CPC .......... *C11B 9/0019* (2013.01); *A01N 25/04* (2013.01); *A01N 65/06* (2013.01); *A01N 65/40* (2013.01); *A61K 9/0014* (2013.01); *A61K 9/107* (2013.01); *A61K 31/59* (2013.01); *A61K 47/10* (2013.01); *A61K 47/44* (2013.01); *C11B 9/0015* (2013.01); *C11D 1/662* (2013.01); *C11D 3/382* (2013.01); *C11D 3/50* (2013.01)

(58) Field of Classification Search
CPC ..... C11B 9/0019; C11B 9/0015; A01N 25/04; A01N 65/06; A01N 65/40; A01N 9/0014; A01N 9/107; A01N 31/59; A01N 47/10; A01N 47/44; C11D 3/50; C11D 1/662; C11D 3/382
USPC .......................................................... 424/400
See application file for complete search history.

(56) References Cited

U.S. PATENT DOCUMENTS

2016/0296430 A1* 10/2016 Das .................... A61K 8/735

OTHER PUBLICATIONS

Hassan S, Adam F, Abu Bakar MR, Abdul Mudalip SK. Evaluation of solvents' effect on solubility, intermolecular interaction energies and habit of ascorbic acid crystals. Journal of Saudi Chemical Society. 2019;23(2):239-248.
Mahakittikun V, Soonthomchareonnon N, Foongladda S, Boitano JJ, Wangapai T, Ninsanit P. A preliminary study of the acaricidal activity of clove oil, Eugenia caryophyllus. Asian Pacific Journal of Allergy and Immunology. 2014;32 (1):46-52.
Quintas V, Prada-López I, Carreira MJ, Suárez-Quintanilla D, Balsa-Castro C, Tomás I. In Situ Antibacterial Activity of Essential Oils with and without Alcohol on Oral Biofilm: A Randomized Clinical Trial. Frontiers in Microbiology. 2017;8:2162. Published Nov. 23, 2017. doi:10.3389/fmicb.2017.02162.

* cited by examiner

*Primary Examiner* — Kristin A Vajda
(74) *Attorney, Agent, or Firm* — Nolan Heimann LLP; Adam Diament

(57) ABSTRACT

The present invention relates to a composition comprising a) at least one oil phase, b) at least one aqueous phase, c) at-least one emulsifier, wherein the at-least one emulsifier is any or combination of at-least one emulsifier agent, water with emulsification properties, oil with emulsification properties, and active ingredient with emulsification properties; and d) optionally, one or more biologically active ingredients. The present invention also relates to use of the composition for personal care, pet care, home care, deodorants, pesticides, moisturizers, disinfectants, cleansers, therapeutic devices, topical supplements and/or nutrition. The present invention also relates to a method for preparing such a composition.

1 Claim, 12 Drawing Sheets

OIL-WATER COMPOSITIONS, METHODS, AND USES THEREOF

CROSS-REFERENCE TO RELATED APPLICATIONS

This Application is a Continuation-in-Part Application and claims priority to U.S. patent application Ser. No. 16/270,606, filed on Feb. 8, 2019. This Application is a Continuation-in-Part and claims priority to U.S. patent application Ser. No. 16/294,852, filed on Mar. 6, 2019. This Application is a Continuation-in-Part and claims priority to U.S. patent application Ser. No. 16/389,935, filed on Apr. 20, 2019. This Application is a Continuation-in-Part and claims priority to U.S. patent application Ser. No. 16/724,296, filed on Dec. 22, 2019.

FIELD

Embodiments of the present disclosure relate to non-toxic and ultra-low toxicity oil-water based emulsions, methods and uses thereof. In particular, embodiments of the present disclosure relate to oil-water emulsions with reduced or eliminated volatile organic compound content, methods for preparation and uses thereof.

DESCRIPTION OF THE RELATED ART

VOCs (volatile organic compounds) are widely used in mass consumer goods to mix oil and water. They are found in products such as fragrances, deodorants, and the like. VOCs are widely known to damage live tissues and have adverse effects on the environment as regulated by OSHA, EPA, and others. Thus, consumer protection and environmental lobbies in various states are working toward enacting legislation which reduces or eliminates the use of VOCs in personal care products. For instance, legislation has been enacted in certain states which limits the amounts of VOCs in aerosol products to 80 percent. It is anticipated that the permitted percent of VOC content in different products will further be reduced with new guidelines.

More recently, evidence or proof exists that VOCs damage active ingredients. The following two references disclose that solvents cause damage to active ingredients, all incorporated by reference in their entireties. Quintas et al, *In Situ Antibacterial Activity of Essential Oils with and Without Alcohol on Oral Biofilm: A Randomized Clinical Trial.* Frontiers in Microbiology (2017); Hassan et al., *Evaluation of Solvents' Effect on Solubility, Intermolecular Interaction Energies and Habit of Ascorbic Acid Crystals.* Journal of Saudi Chemical Society (2019). The environmental detriment towards damage to limited resources such as essential oils, and the prospect of maintaining the active state of substances is also of significance.

If VOCs are reduced or removed from products, other constituents must be substituted in their place to mix oil and water. There are few nonvolatile liquids which would be suitable, and of those, few have been utilized successfully to fully replace VOCs. More commonly, the elimination of VOCs often coincides with oil-only and/or aqueous-only solutions.

Eliminating or reducing VOCs in anhydrous systems or moving into low VOC content aqueous-based systems involves changes with the behavior and appearance of formulations. For example, if VOCs are reduced in the traditional anhydrous systems, they must be replaced with some suitable non-VOC ingredient. If that ingredient is water, the result is an aqueous-based solution, and the traditional water insoluble resins must be replaced with water soluble resins. However, it has been found that limiting products to water soluble components only are commercially unsatisfactory. Furthermore, resins are difficult to homogenize, manufacture, and use with containers, often clogging the spray nozzle or causing other malfunctions.

There is thus a need for compositions that replace and/or eliminate the use of VOCs and yet provide an aesthetically pleasing commercial product that is easy to use and effective at homogenizing oil and water-soluble components in a manner that does the least amount of damage to live tissues and bioactive substances.

SUMMARY

Oil-water emulsions with reduced or eliminated VOC content, method and uses of the composition are described. According to an embodiment, a composition comprising a) at least one oil phase, b) at least one aqueous phase, c) at-least one emulsifier, wherein the at-least one emulsifier is any or combination of at-least one emulsifier agent, water with emulsification properties, oil with emulsification properties, and active ingredient with emulsification properties; and, optionally, one or more biologically active ingredients.

In one specific embodiment, the at least one oil phase is an aromatic essential oil having innate anti-pesticidal and anti-inflammatory properties and is between 5% and 50% of a total weight of the composition. The at least one aqueous phase is comprised of distilled water that is a distillation product derived from of at least one of rose water, peppermint, frankincense, cumin, and orange blossom water. The at least one aqueous phase is comprised of a salt, and the at least one aqueous phase is between 50% of 95% by weight of the composition. The aqueous phase may be one of at least non-distilled water, distilled water, ocean water, tea, or coffee. The at least one emulsifier includes at least one of polysorbate and polyethylene glycol (PEG). The at least one emulsifier is between 0% and 5% of the total weight of the composition. The at least one emulsifier may be present in at least trace amounts, i.e., between 0.01% and 5% of the total weight of the composition. The one or more biologically active ingredients is comprised of a biochemical macromolecule that includes at least one of vitamins, antioxidants, polyphenols, terpenoids, flavonoids, carotenoids, cannabinoids, alpha-hydroxy acids, beta-hydroxy acids, organic peroxides, and amino acids. The one or more biologically active ingredients is between 5% and 50% of the total weight of the composition.

According to another embodiment, there is a method wherein the composition comprises the step of administering the above referenced composition(s), or any of the compositions described in the detailed description of the embodiments below.

According to yet another embodiment there is a method of preparing the composition described above (or below in the detailed description of the embodiments) comprising homogenization of at least one oil phase and at least one aqueous phase.

Embodiments of the present disclosure provides different applications of the composition for personal care, pet care, home care, deodorants, fragrances, pesticides, moisturizers, disinfectants, cleansers, therapeutics, topical supplementation and/or nutrition.

An embodiment of the present disclosure provides a method for preparing a composition, the composition forms a homogenous stable oil-in-water intermediary product comprising full or partial homogenization of a mixture of oil in water for a limited time period after using physical mechanics. The appearance of the composition is unique with the oil and water layers clearly separated at stasis.

The compositions and methods can aid in reduction of rashes, aid in wound health, improve neurological function, can be used as a treatment for bacterial infections, fungal infections, and autoimmune disorders.

BRIEF DESCRIPTION OF THE DRAWINGS

In the figures, similar components and/or features may have the same reference label. Further, various components of the same type may be distinguished by following the reference label with a second label that distinguishes among the similar components. If only the first reference label is used in the specification, the description applies to any one of the similar components having the same first reference label irrespective of the second reference label.

DETAILED DESCRIPTION

Figure 1:
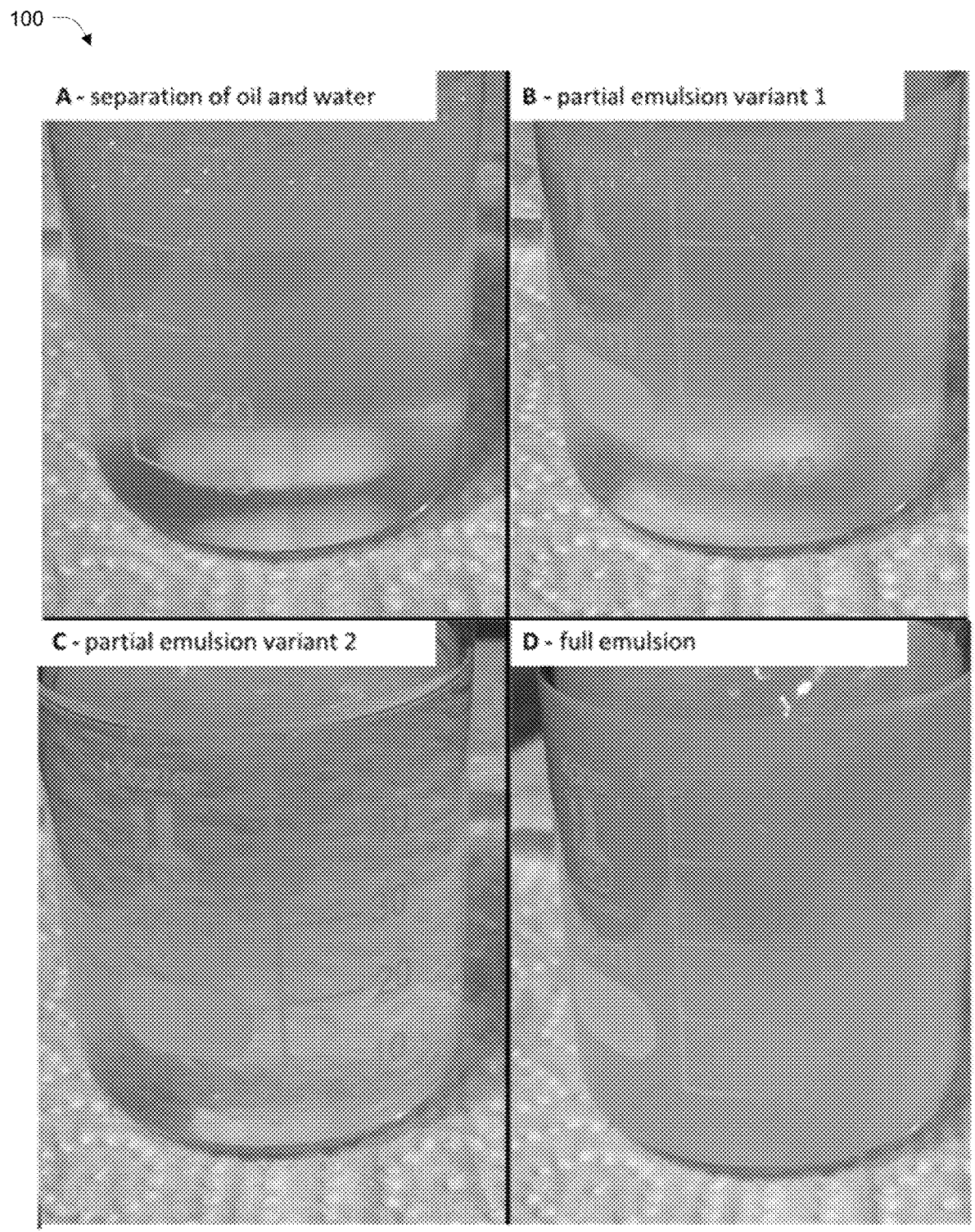
FIG. 1 shows the preparation of composition.

The materials, compounds, compositions, articles, and methods described herein may be understood more readily by reference to the following detailed description of specific aspects of the disclosed subject matter and the Examples included therein.

General Definitions

In this specification and in the claims that follow, reference will be made to a number of terms, which shall be defined to have the following meanings:

All percentages, ratios and proportions herein are by weight, unless otherwise specified. All temperatures are in degrees Celsius (degrees C.) unless otherwise specified.

The terms "a" and "an" are defined as one or more unless this disclosure explicitly requires otherwise.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

The terms "comprise" (and any form of comprise, such as "comprises" and "comprising")," have" (and any form of have, such as "has" and "having"), "include" (and any form of include, such as "includes" and "including") and "contain" (and any form of contain, such as "contains" and "containing") are open-ended linking verbs. As a result, an apparatus that "comprises," "has," "includes," or "contains" one or more elements possesses those one or more elements but is not limited to possessing only those elements. Likewise, a method that "comprises," "has," "includes," or "contains" one or more steps possesses those one or more steps but is not limited to possessing only those one or more steps.

Any embodiment of any of the disclosed methods or compositions can consist of or consist essentially of rather than comprise/include/contain/have any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

Any embodiment of any of the disclosed compounds or methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

The present invention relates to a composition comprising at least one oil phase, at least one aqueous phase, at-least one emulsifier, wherein the at-least one emulsifier is any or combination of at-least one emulsifier agent, water with emulsification properties, oil with emulsification properties, and active ingredient with emulsification properties; and, optionally, one or more biologically active ingredients.

In one aspect, the emulsification properties exist or are added in oil phase. In another aspect, the emulsification properties exist or are added in aqueous phase. In one aspect, the emulsification properties exist or are added in oil phase and/or aqueous phase are each characterized as being emulsifying or non-emulsifying. As a general matter, the emulsifier may be 1) an emulsifying agent to add to an oil-water mixture, 2) an emulsifying water preparation (e.g., salt water preparation, distillation products such as rose water, orange water, peppermint water, etc.), 3) an emulsifying oil preparation (e.g. polysorbate-oil preparation), 4) a naturally emulsifying water (e.g., ocean water), 5) a naturally emulsifying oil (e.g., beeswax), or 6) an active ingredient with emulsification properties (e.g. salicylic acid).

With respect to the distillation products, the aqueous distillates are the water component of compound distillations. The solutions under distillation (complex organic macromolecular materials) are emulsifying to varying degrees, and the product of the water after distillation is also emulsifying to varying degrees, and may be further enhanced by the addition of ions (salt), peroxides, and esterified fatty acid or like molecules at very low concentrations.

Aqueous emulsions mix oil and water to varying degrees and may be naturally occurring or prepared. Naturally occurring aqueous emulsions include ocean water, distilled water, urine, serum, saliva, and hydrogen peroxide. Other prepared aqueous emulsions include coffee, tea, beer, wine, salt water preparations, and other aqueous distillates.

In one aspect of the method of adding an emulsifying agent, an oil and water preparation is added to a holding vessel. Neither the oil or water layers are emulsifying. Without the addition of the emulsifying agent, oil droplets in water would exist without any form of homogenization. An emulsifying agent (such as polysorbate) may be added drip wise until the oil and water homogenize partially or completely. The resulting solution will therefore be a homogenization of oil and water.

In one aspect, the composition is an oil-in-aqueous type composition. In one aspect, the composition comprises water in the aqueous phase. The aqueous phase may comprise water such as distilled water, salt water, ocean water and/or distilled water (e.g. rose water). The blend ratio is the balance of the ingredients other than water; it is generally in the range of 5-50 wt %. The aqueous phase that is present in a content ranging from 50 percent to 95 percent by weight relative to the total weight of the composition. The aqueous phase may further have emulsifying properties.

In one aspect, the composition includes the oil-phase, which includes one or more oils. The composition comprising the oil-phase includes the oil selected from the group consisting of volatile oils, non-polar oils; non-volatile oils, polar oils; non-volatile, non-polar oils; non-volatile paraffinic hydrocarbon oils; and mixtures thereof. The oil may be of plant or non-plant origin, preferably such as vegetable oil, cedarwood oil and/or fish oil. The oil phase may further have emulsifying properties.

The oil phase comprising the oils includes one or more esterified fatty acids and derivatives. The fatty acid portion of said fatty acid usually has 4-22 carbon atoms, preferably 4-10. Examples of the fatty acid that is added to this emulsified composition include sodium laurate, sodium myristate, sodium palmitate, sodium stearate, sodium oleate, potassium laurate, potassium myristate, potassium palmitate, potassium stearate, potassium oleate, polyethylene glycol, polyoxyethylene sorbitan monooleate, monoethanolamine laurate, monoethanolamine myristate, monoethanolamine palmitate, and monoethanolamine stearate.

In one aspect, the blend ratio of fatty acids thus added to this composition is not limited in particular and can be chosen according to the specific form of this emulsified composition and other ingredients. Generally, the fatty acid has 4-22 carbon atoms and the blend ratio is 0-5.0 wt % of the composition, and preferably the fatty acid has 4-10 carbon atoms and the blend ratio is approximately 0-4.0 wt % of the composition. The composition comprising the oil-phase is present in a content ranging from 5 to 50 percent by weight relative to the total weight of the composition.

In one aspect, the emulsifying agent is added in oil phase. In one aspect, the emulsifying agent is added in aqueous phase. In one aspect, the emulsifying agent is added in oil phase and/or aqueous phase. The emulsifier present in the composition is selected from the group consisting of surfactants, soap, detergents. In one aspect, the surfactant is an anionic, cationic, nonionic, or amphoteric surfactant. In one aspect, the surfactant is a water-soluble surfactant.

In one aspect, composition according to the invention comprises at least one surfactant. Surfactants are compounds, which reduce the surface tension of water. Examples of surfactants are ionic (anionic or cationic) and nonionic surfactants. Usually, the composition according to the invention comprises at least one surfactant, i.e. one, two, three or more surfactants.

The preferred surfactants are hydrophilic and are further characterized as being water-soluble. Any hydrophilic-type surfactant such as ethoxylated nonyl phenols, ethoxylated nonyl phenol formaldehyde resin, dioctyl esters of sodium sulfosuccinate, and octyl phenol polyethoxylated ethanol can be used.

Other surfactants that may be employed include the soaps such as sodium and potassium myristate, laurate, palmitate, oleate, stearate, resinate, and hydroabietate, the alkali metal alkyl or alkylene sulfates, such as sodium lauryl sulfate, potassium stearyl sulfate, the alkali metal alkyl or alkylene sulfonates, such as sodium lauryl sulfonate, potassium stearyl sulfonate, and sodium cetyl sulfonate, sulfonated mineral oil, as well as the ammonium salts thereof; and salts of high means like lauryl amine hydrochloride, and stearyl amine hydrobromide.

Any anionic, cationic, or nonionic compound can be used as the surfactant.

Examples of suitable anionic surfactants are alkali metal, ammonium and amine soaps; the fatty acid part of such soaps. Other examples of suitable anionic surfactants are alkali metal salts of alkyl-aryl sulfonic acids, sodium dialkyl sulfosuccinate, sulfated or sulfonated oils, e.g., sulfated castor oil; sulfonated tallow, and alkali salts of short chain petroleum sulfonic acids.

Examples of suitable cationic surfactants are salts of long chain primary, secondary, or tertiary amines, such as oleylamine acetate, cetylamine acetate, di-dodecylamine lactate, the acetate of aminoethyl-aminoethyl stearamide, dilauroyl triethylene tetramine diacetate, 1-aminoethyl-2-heptadecenyl imidazoline acetate; and quaternary salts, such as cetylpyridinium bromide, hexadecyl ethyl morpholinium chloride, and diethyl di-dodecyl ammonium chloride.

Examples of suitable nonionic surfactants are condensation products of higher fatty alcohols with ethylene oxide, such as the reaction product of oleyl alcohol with ethylene oxide units; condensation products of alkylphenols with ethylene oxide, such as the reaction products of isooctylphenol with 12 ethylene oxide units; condensation products of higher fatty acid amides with 5, or more, ethylene oxide units; polyethylene glycol esters of long chain fatty acids, such as tetraethylene glycol monopalmitate, hexaethyleneglycol monolaurate, nonaethyleneglycol monostearate, nonaethyleneglycol dioleate, tridecaethyleneglycol monoarachidate, tricosaethylene glycol monobehenate, tricosaethyleneglycol dibehenate, polyhydric alcohol partial higher fatty acid esters such as sorbitan tristearate, ethylene oxide condensation products of polyhydric alcohol partial higher fatty esters, and their inner anhydrides (mannitol-anhydride, called mannitan, and sorbitol-anhydride, called sorbitan), such as glycerol monopalmitate reacted with 10 molecules of ethylene oxide, pentaerythritol monooleate reacted with 12 molecules of ethylene oxide, sorbitan monostearate reacted with 10 to 15 molecules of ethylene oxide; long chain polyglycols in which one hydroxyl group is esterified with a higher fatty acid and the other hydroxy group is esterified with a low molecular alcohol, such as methoxypolyethylene glycol 550 monostearate (550 meaning the average molecular weight of the polyglycol ether). A combination of two or more of these surfactants may be used; e.g. a cationic may be blended with a nonionic or an anionic with a nonionic. Following is a list of suitable surfactants that could be used in the practice of this invention. Any water-soluble surfactant could be used, but naturally some are more efficient than others.

Useful surfactants include, but are not limited to: polyoxyethylene alkyl phenol, polyoxyethylene (10 mole) cetyl ether, polyoxyethylene alkylaryl ether, polyoxyethylene monolaurate, polyoxyethylene vegetable oil, polyoxyethylene sorbitan monolaurate, polyoxyethylene esters or mixed fatty and resin acids, poly oxyethylene sorbitol lanolin derivative, polyoxyethylene (12 mole) tridecyl ether, polyoxyethylene sorbitan esters of mixed fatty and resin acids, polyoxyethylene sorbitan monostearate, polyoxyethylene sorbitan monooleate, polyoxyethylene monostearate, polyoxyethylene (20 mole) stearyl ether, polyoxyethylene (20 mole) oleyl ether, polyoxyethylene (15 mole) tridecyl ether, polyoxyethylene fatty alcohol, polyoxyethylene alkyl amine, polyoxyethylene glycol monopalmitate, polyoxyethylene sorbitan monopalmitate, polyoxyethylene (20 mole) cetyl ether, polyoxyethylene oxypropylene stearate, polyoxyethylene lauryl ether, polyoxyethylene lanolin derivative, sodium oleate, quaternary ammonium derivative, potassium oleate, N-cetyl N-ethyl morpholinium ethosulfate, and pure sodium lauryl sulfate.

In addition to using the water-soluble surfactants described above, other surfactants may be used such as silicones, clays and the like which are included as surfactants since, in certain instances, they tend to invert the emulsion even though they are not water-soluble. In other specific cases the surfactant may be directly added to the polymer-containing emulsion; thereby rendering it self-inverting upon contact with water.

In a preferred aspect, the emulsifier is selected from a group consisting of: polysorbate 20, 60, and 80, polyethylene glycol 200, 400, 600, and 1000, ocean water, distilled products (e.g. rose water), ionized water, salt water preparations, coffee, tea, beeswax, and tocopheryl acetate.

In one aspect, the total amount of emulsifying agent in the composition greater than 0% or at most 4% total weight of the composition.

In one aspect, the emulsifying agent can be any naturally emulsifying compound including, and not limited to, ocean water, tocopherol, beeswax, fermented products, coffee, tea, distilled water and/or aqueous products of distillation, and biochemical macromolecules including bacterial cells, proteins, nucleic acids, polyphenols, and others including bioactive or active substances.

In one aspect, the natural separation of oil and water layers 100 as shown in FIG. 1A. The intensity of the emulsification depends on the concentrations and types of emulsifiers. In one aspect, 1% total concentration of two different fatty acid like emulsifiers resulted in a difference of appearance that was partial emulsification. One variation retains a separated oil layer with decreased thickness or volume, and an emulsion that is less translucent with respect to a separated state of the suspension as shown in FIG. 1B. The other variation results in a total incomplete emulsion or nanoemulsion as shown in FIG. 1C. A higher concentration will yield a fully emulsified product that is homogeneous and non-translucent as shown in FIG. 1D.

Figure 2:
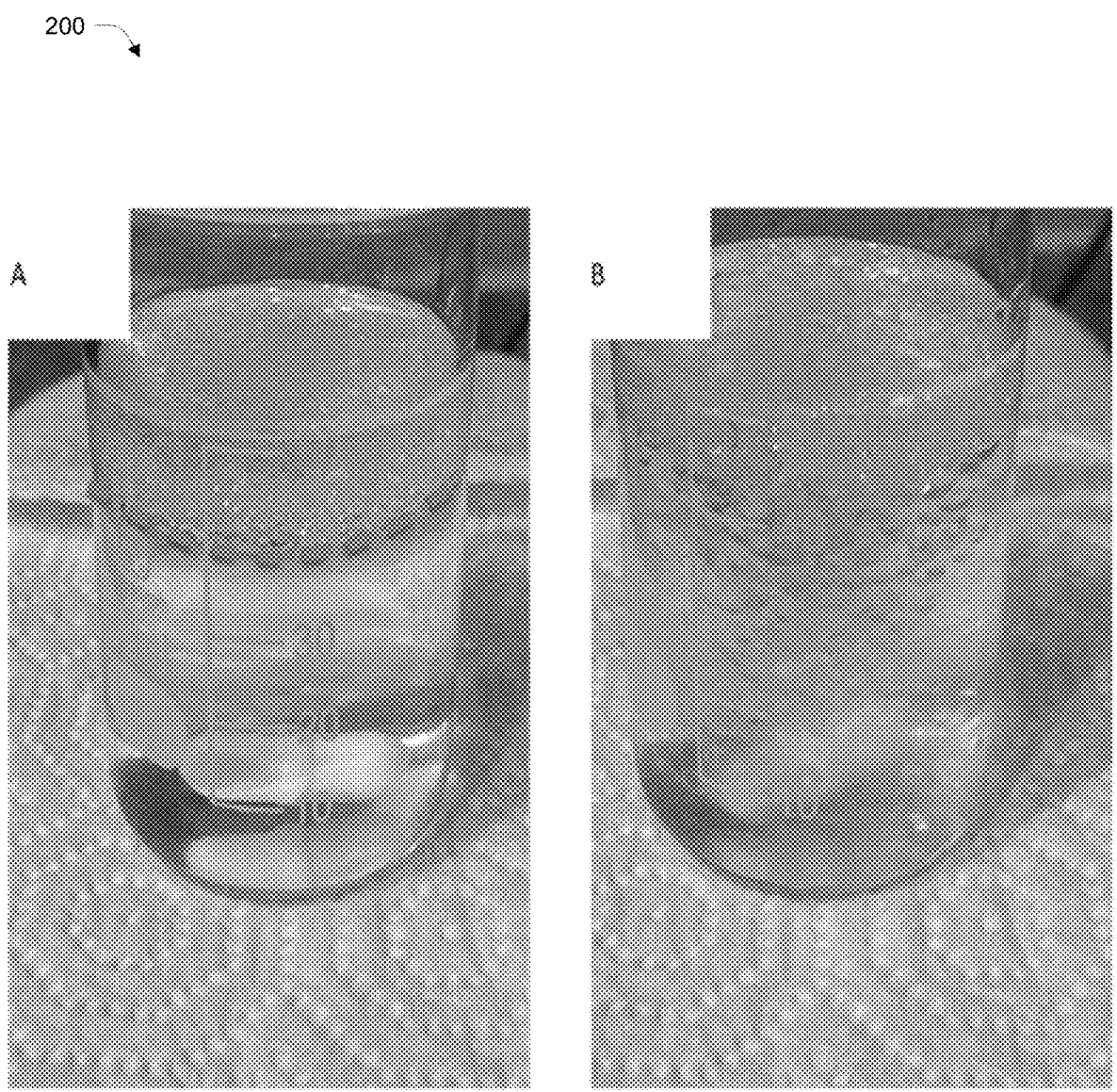
FIG. 2 shows the emulsification of oil and water in the absence of emulsifiers and solvents.

In one aspect, the emulsification of oil and water 200 in the absence of emulsifiers and solvents as shown in FIG. 2. In its settled state, the oil and water layers are separated as shown in FIG. 2A. Upon mechanical stirring, the oil and water layers do not mix, and form oil droplets in water as shown in FIG. 2B. In the absence of emulsifiers and/or solvents, the composition is not emulsified, and the oil and water separation are instantaneous.

Figure 3:
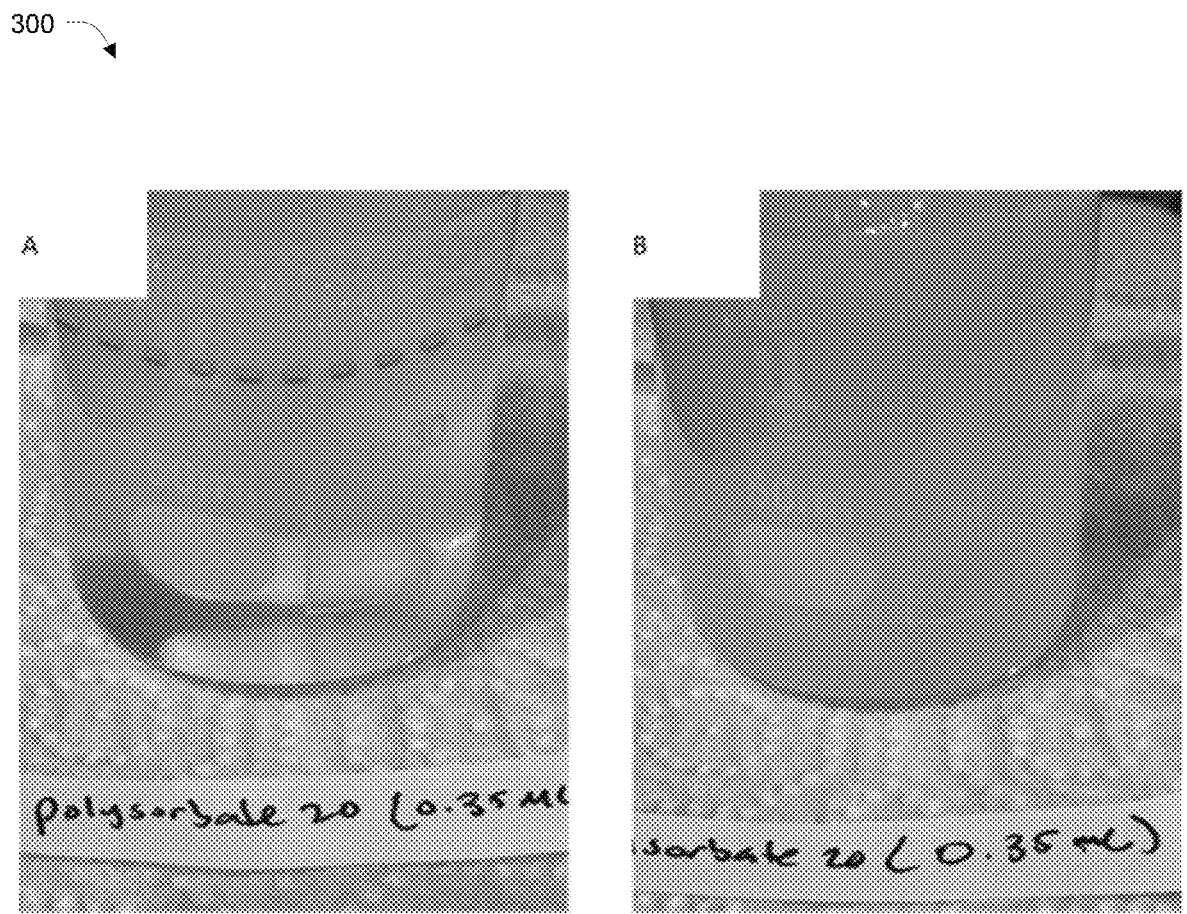
FIG. 3 shows layers of emulsification of oil and water.

In one aspect, there is complete emulsification of oil and water 300 with 0.7% total weight polysorbate 20. In its settled state the oil and water layers remain separated as shown in FIG. 3A. Upon mechanical stirring, the oil and water layers mix to form a full emulsion, a homogeneous and/or phased non-translucent product and/or state as shown in FIG. 3B.

Figure 4:
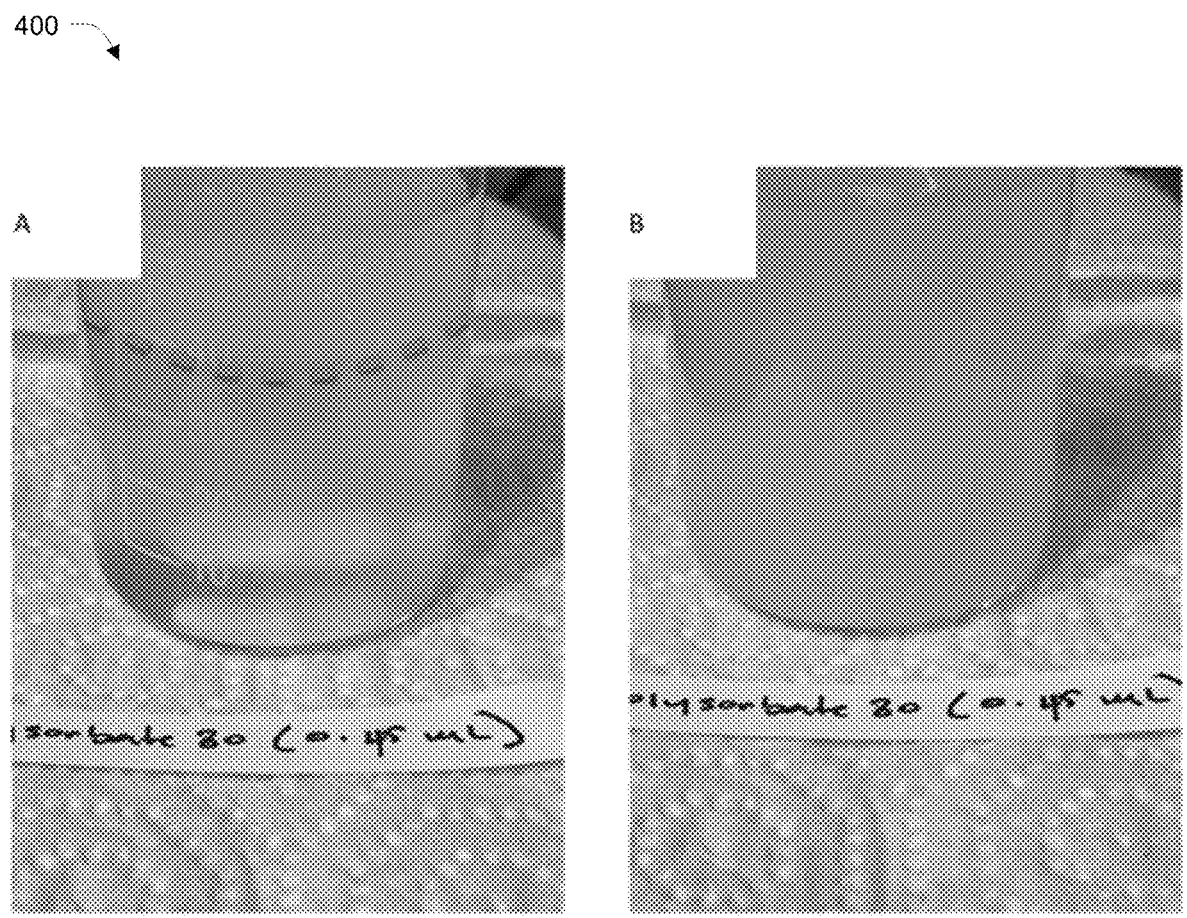
FIG. 4 shows homogeneous emulsification of oil and water with low or ultra-low volume addition of polysorbate.

In one aspect, there is complete emulsification of oil and water 400 with 0.9% total weight polysorbate 80. In its settled state the oil and water layers remain separated as shown in FIG. 4A. Upon mechanical stirring, the oil and water layers mix to form a full emulsion, a homogeneous and/or phased non-translucent product and/or state as shown in FIG. 4B.

Figure 5:
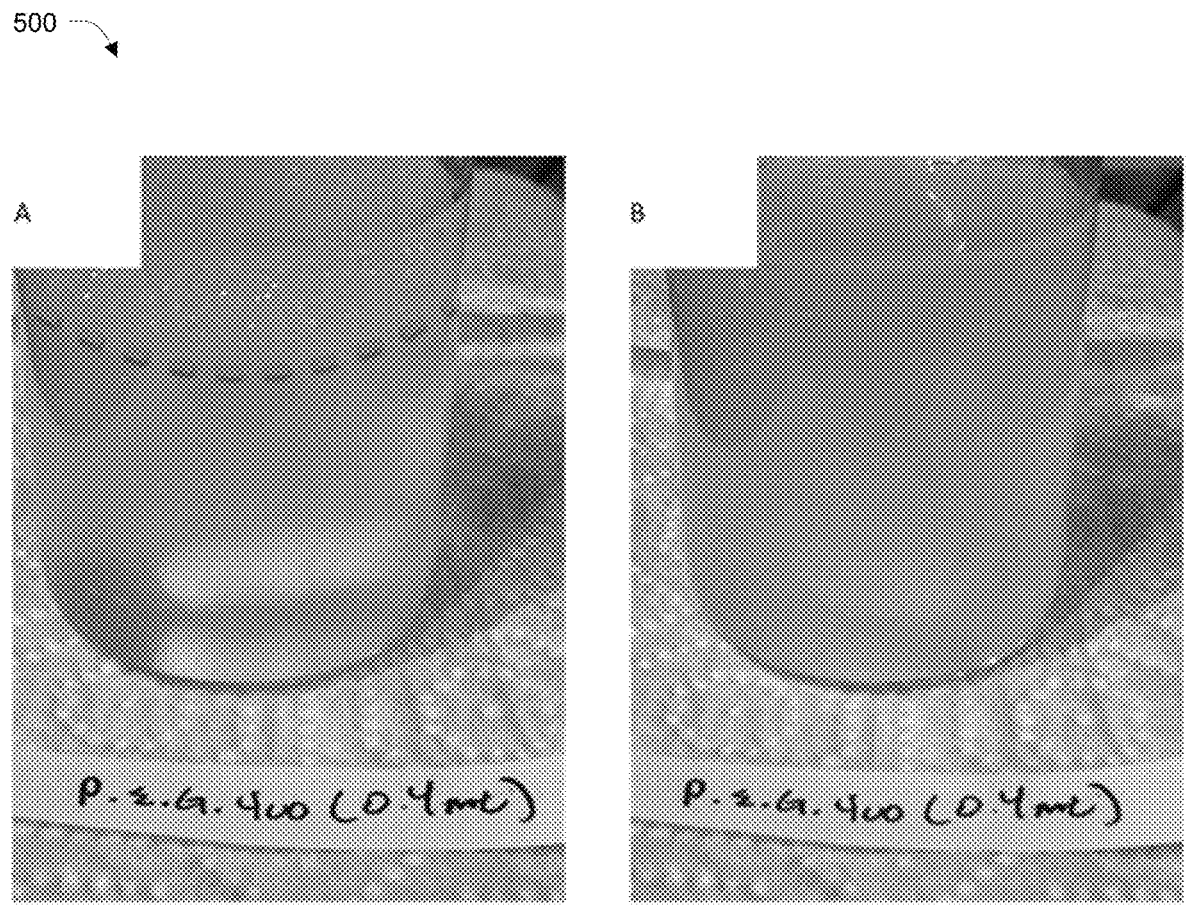
FIG. 5 shows homogeneous emulsification of oil and water with low or ultra-low volume addition of polyethylene glycol.

In one aspect, the emulsification of oil and water 500 with 0.8% total weight polyethylene glycol 400. In its settled state, the oil and water layers remain separated as shown in FIG. 5A. Upon mechanical action (stirring), the oil and water layers mix to form a full emulsion, a homogeneous and/or phased non-translucent product and/or state as shown in FIG. 5B.

Figure 6:
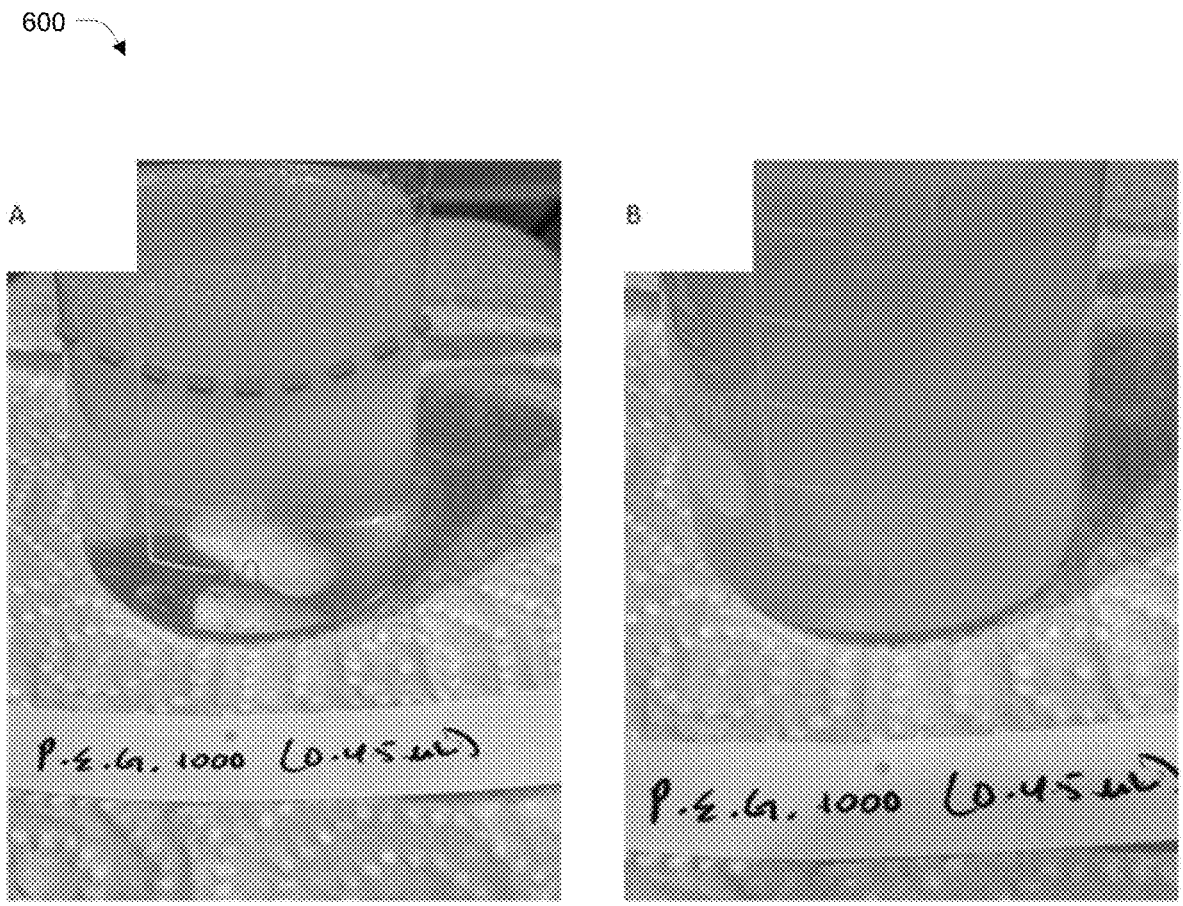
FIG. 6 shows homogeneous emulsification of oil and water with low or ultra-low volume addition of polyethylene glycol 1000.

In one aspect, there is complete emulsification of oil and water 600 with 0.9% total weight tocopherol polyethylene glycol 1000. In its settled state, the oil and water layers remain separated as shown in FIG. 6A. Upon mechanical stirring, the oil and water layers mix to form a full emulsion, a homogeneous and/or phased non-translucent product and/or state as shown in FIG. 6B.

Figure 7:
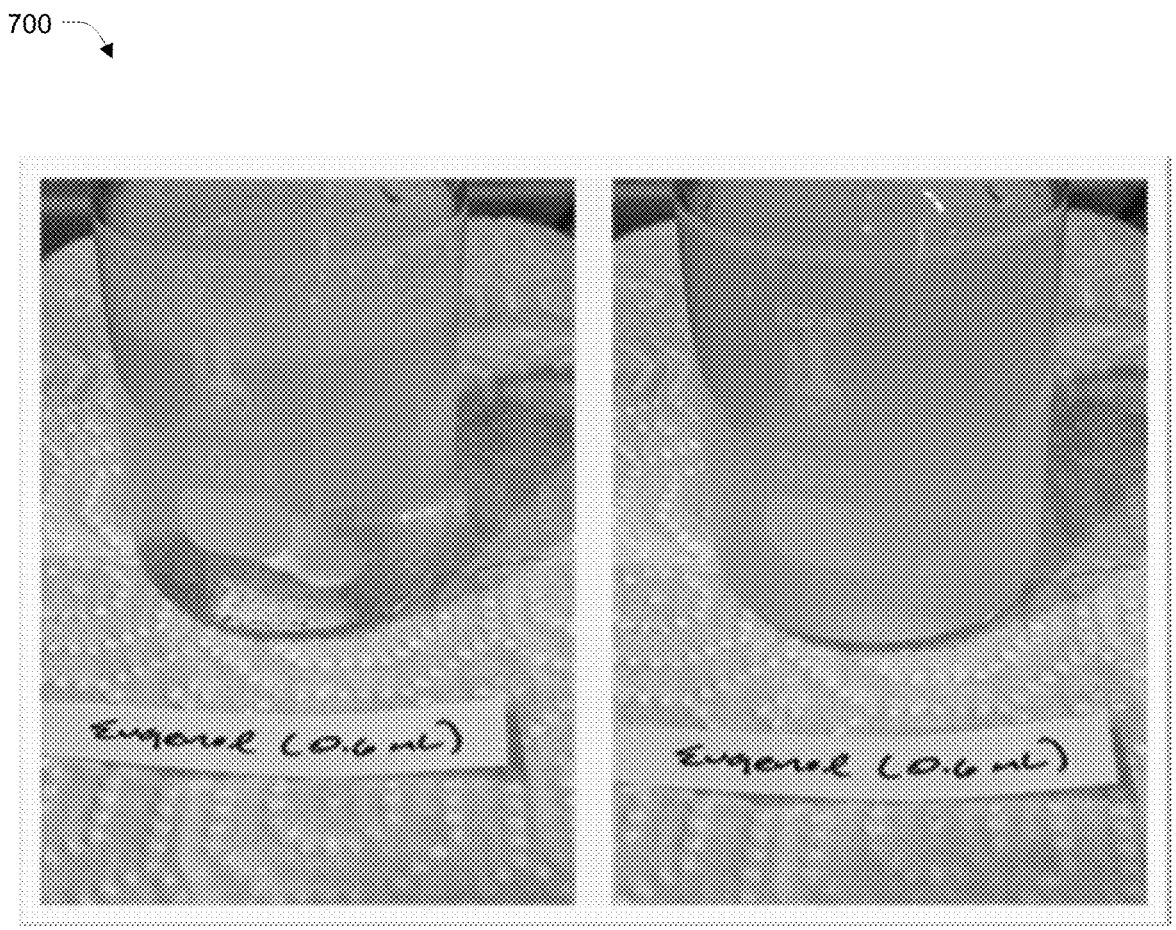
FIG. 7 shows homogeneous emulsification of oil and water with low or ultra-low volume addition of eugenol.

In one aspect, there is complete emulsification of oil and water 700 with 1.2% total weight eugenol. In its settled state the oil and water layers remain separated as shown in FIG. 7A. Upon mechanical stirring, the oil and water layers mix to form a full emulsion, a homogeneous and/or phased non-translucent product and/or state as shown in FIG. 7B.

Figure 8:
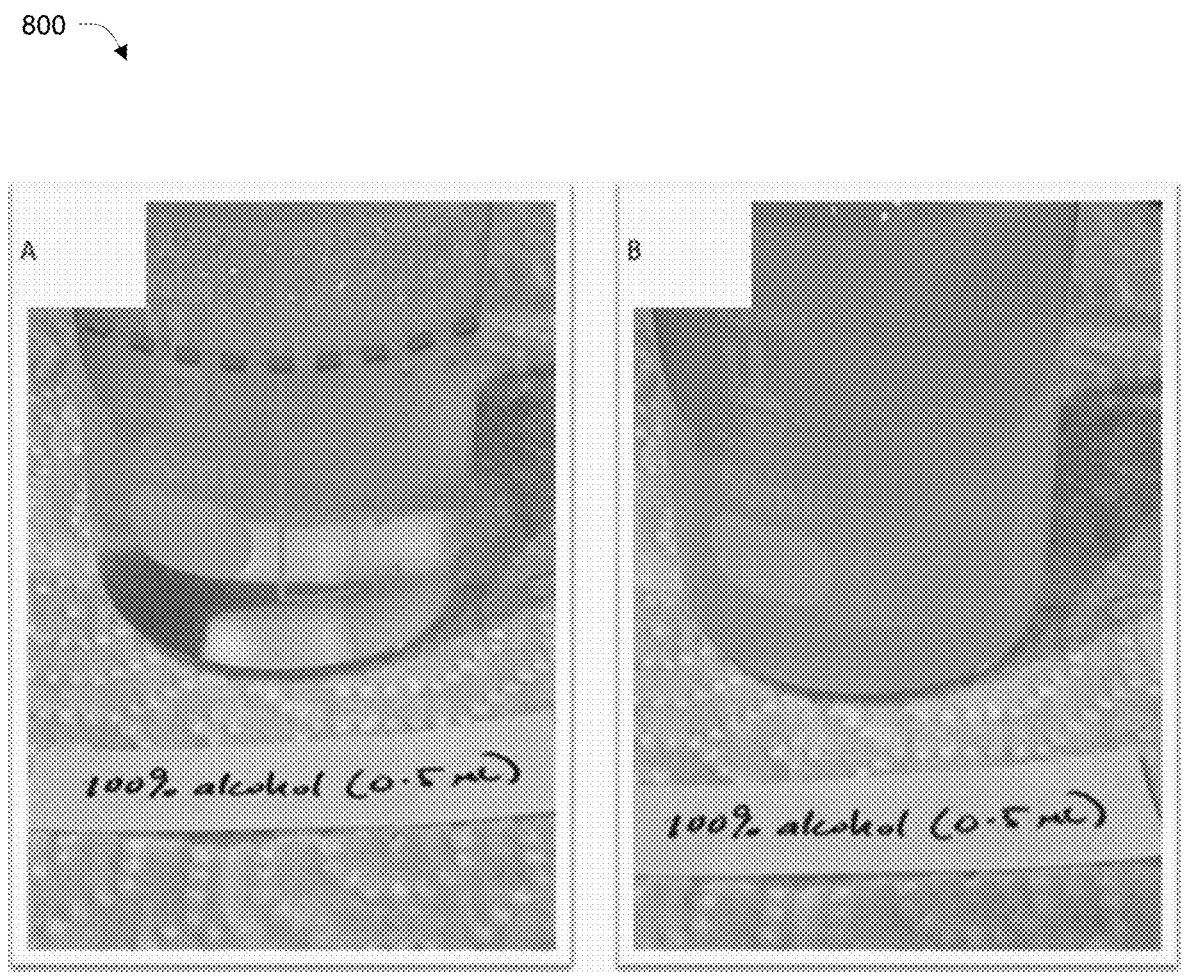
FIG. 8 shows homogeneous emulsification of oil and water with low or ultra-low volume addition of alcohol.

In one aspect, the complete emulsification of oil and water 800 with 1.0% total weight denatured alcohol consisting of equal or near equal parts ethanol and methanol. In its settled state the oil and water layers remain separated as shown in FIG. 8A. Upon mechanical stirring, the oil and water layers form a fully emulsified non-translucent product and/or state as shown in FIG. 8B.

Figure 9:
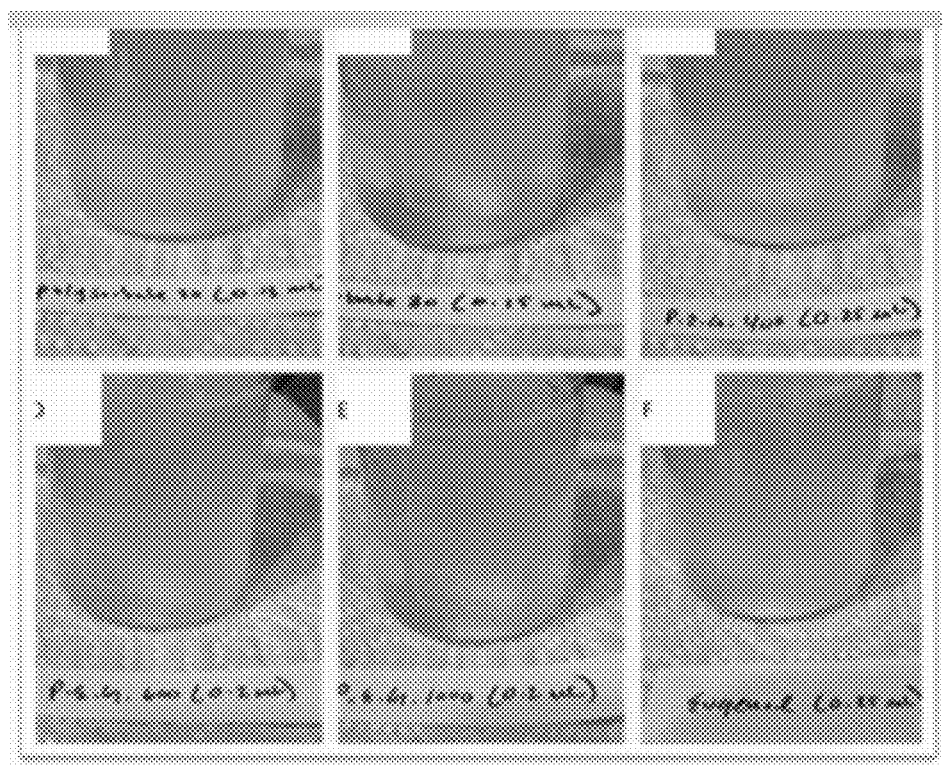
FIG. 9 shows comparative homogenization with low or ultra-low volume addition of emulsifier across polysorbates, polyethylene glycols, and eugenol.

In one aspect, the emulsification polysorbates 900 as shown in FIGS. 9A and 9B, polyalkylenes as shown in FIGS. 9C, 9D, and 9E, and solvents as shown in FIG. 9F at near similar or identical minimal concentrations. Note the incomplete mixture of oil and water whereby the product is semi-non-translucent.

Figure 10:
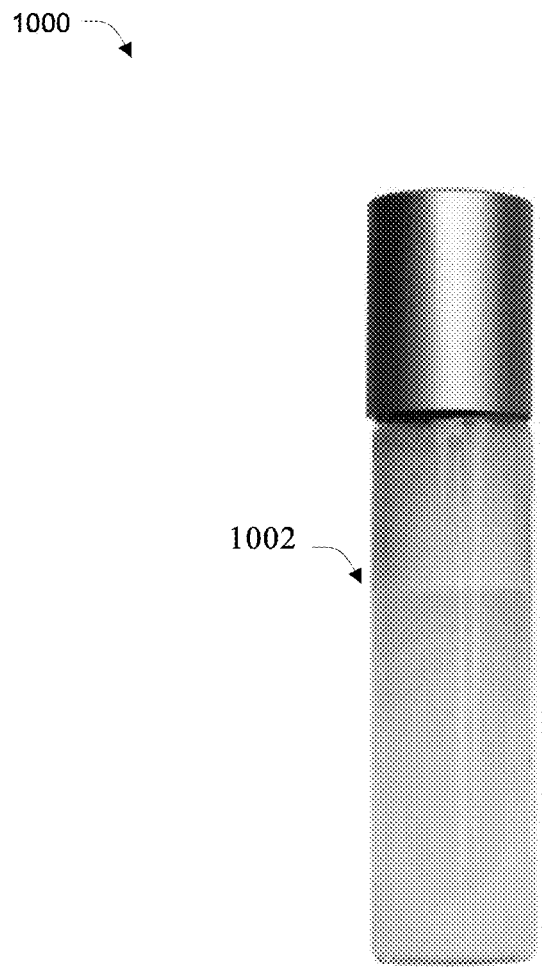
FIG. 10 shows the unique appearance non-homogenized layers at stasis with a clear separation of oil and water layers.

In one aspect, the visually distinguishable appearance of the products of the current invention. There is a separation of oil and water layers 1000 that may mix and/or homogenize after shaking, spinning, or other mechanical agitation as shown in FIG. 10. The mixing apparatus can be any type of container, and may allow for mechanical shaking, stirring, sonication, and spinning, or may be a container that can mix ingredients based on electrical, radio or other types of energy to induce mixing of molecules. The oil-water delineating region 1002 is shown as an example to illustrate the retention of the natural separation of oil from water (pre-homogenization).

In one aspect, the chemical representation of salicylic acid as a solvent. When preparations contain active ingredients for topical skin care or therapeutics, such as salicylic acid, they may have the potential to contribute to the mixture of oil and water layers, thereby reducing the amounts of other emulsifiers.

In one aspect, the ionization of water through salts, metals, and ions may be delivered within the solution or through the application of an electric current to the water through controlled means. The ionization facilitates mixture of oil and water and would reduce the minimum effective concentrations of esterified emulsions.

In one aspect, the composition optionally further comprises one or more biologically active ingredients.

The biologically active ingredient is selected from the group consisting of live or dead cells, bacteria, viruses, fungi, salts, salicylic acid, chlorpyrifos metals, and components of thereof including proteins, carbohydrates, lipids, nucleic acids, and other chemical macromolecules.

In one aspect, the composition further comprises a biological material.

The material is a macro- or nano-molecular arrangement of substances as partial, one, few, or many layers in medium.

Examples: Gelatin, PLA, PLGA, Graphene, Polymers, Biologics, Metals, and Others

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecyl sulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $Ci_{-4}$ alkyl group), and the like.

In one aspect, the composition further comprises a polymer or acrylates and other graphical carbon molecules as a nano-material and/or at ultra low concentrations.

In one aspect, the polymer is selected from the group consisting of vinyl acetate/crotonates/vinyl neodecanoate copolymer, octylacrylamide/acrylates/butylaminoethyl methacrylate copolymer, vinyl acetate/crotonates, polyvinylpyrrolidone (PVP), polyvinylpyrrolidone/vinyl acetate copolymer, PVP acrylates copolymer, vinyl acetate/crotonic acid/vinyl proprionate, acrylates/acrylamide, acrylates/octylacrylamide, acrylates copolymer, acrylates/hydroxyacrylates copolymer, and alkyl esters of polyvinylmethylether/maleic anhydride, diglycol/cyclohexanedimethanol/isophthalates/sulfoisophthalates copolymer, vinyl acetate/butyl maleate and isobornyl acrylate copolymer, vinylcaprolactam/PVP/dimethylaminoethyl methacrylate, vinyl acetate/alkylmaleate half ester/N-substituted acrylamide terpolymers, vinyl caprolactam/vinylpyrrolidone/methacryloamidopropyl trimethylammonium chloride terpolymer, methacrylates/acrylates copolymer/amine salt, polyvinylcaprolactam, polyurethanes, polyquaternium-4, polyquaternium-10, polyquaternium-11, polyquaternium-46, hydroxypropyl guar, hydroxypropyl guar hydroxypropyltrimmonium chloride, polyvinyl formamide, polyquaternium-7, and hydroxypropyltrimmonium chloride guar.

In one aspect, the composition is administered to a subject. The term "subject" means any animal, in particular mammals including humans but may be other mammals such as dogs.

In one aspect, the composition is administered to the subject selected from different administration delivery systems.

In one aspect, the administration typically is selected from oral, intravenous, subcutaneous, parenteral, intraperitoneal, rectal, vaginal, and/or topical delivery system.

In one aspect, the composition is substantially solvent-free.

In certain embodiments, the composition can be formulated to be a personal care composition, a deodorant, a fragrance, a body wash, a shower gel, a liquid hand cleanser, a pesticide, a shampoo, a conditioner, a bar soap, a home care composition, a hard surface cleaner, a topical supplement, a nutrition supplement, a dish liquid, a therapeutic vehicle, or a fabric conditioner.

In one aspect, the present invention relates to a use of the composition.

In one aspect, the composition can be used as a personal care composition, a deodorant, a fragrance, a body wash, a shower gel, a liquid hand cleanser, a pesticide, a shampoo, a conditioner, a bar soap, a home care composition, a hard surface cleaner, a topical supplement, a nutrition supplement, a dish liquid, a therapy, or a fabric conditioner. FIG. 10 shows homogeneous emulsification of oil and water using different homogenization techniques.

Figure 11:
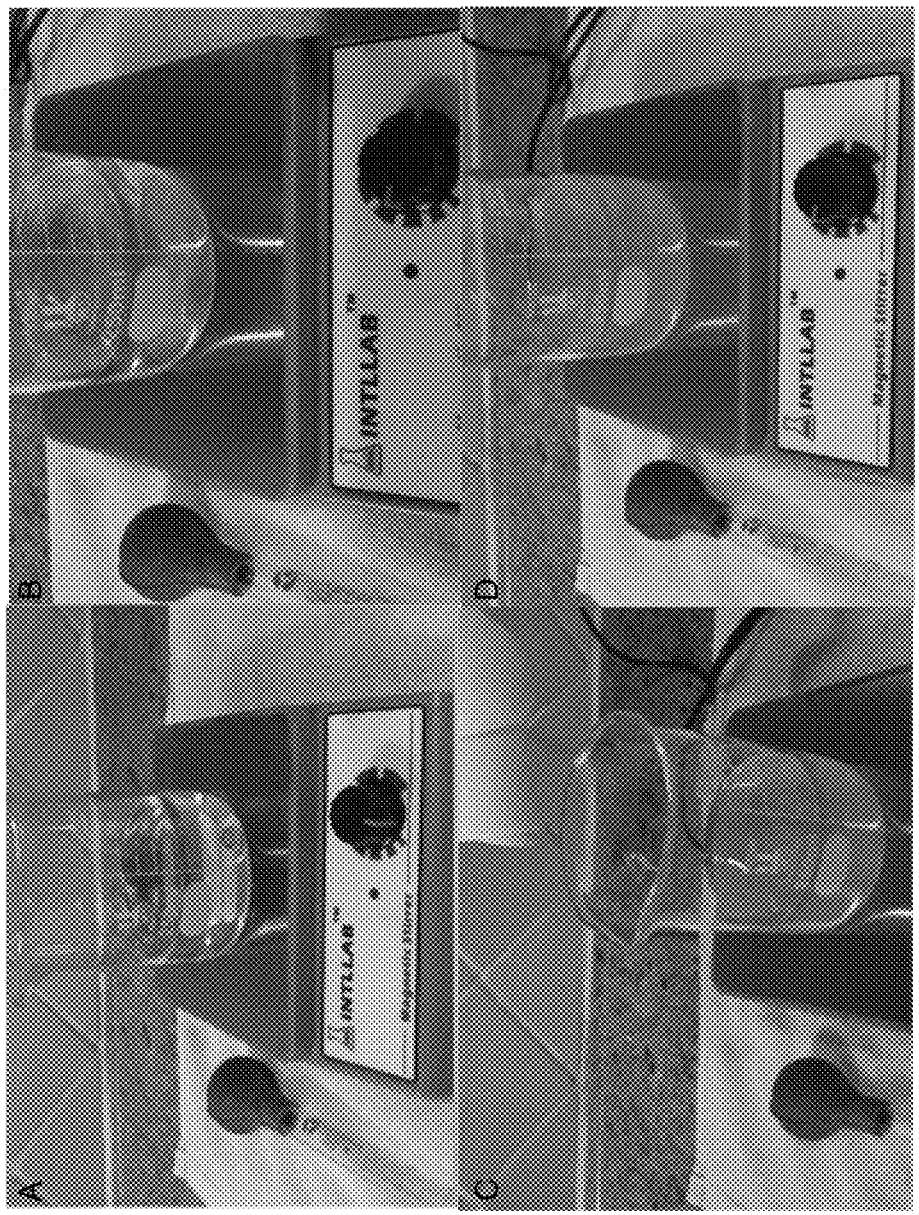
FIG. 11 shows homogeneous emulsification using a method for preparing a composition comprising homogenization of a mixture of oil in aqueous phase.

In one aspect, the present invention relates to a method for preparing a composition comprising homogenization of a mixture of oil in aqueous phase 1100. FIG. 11 shows homogeneous emulsification using a method for preparing a composition comprising homogenization of a mixture of oil in aqueous phase. An oil and water preparation is added to a holding vessel. Without the addition of an emulsifying agent, the oil and water are visually distinct, as seen at FIG. 11A, and there is no appearance of homogenization, as seen in FIG. 11B. An emulsifying agent, for example polysorbate is added dropwise until the oil and water is homogenized, as seen in FIG. 11C. The resultant product is a fully homogenized oil-water solution made with the least amount of added emulsifier to achieve the desired state of emulsification as seen in FIG. 11D.

Figure 12:
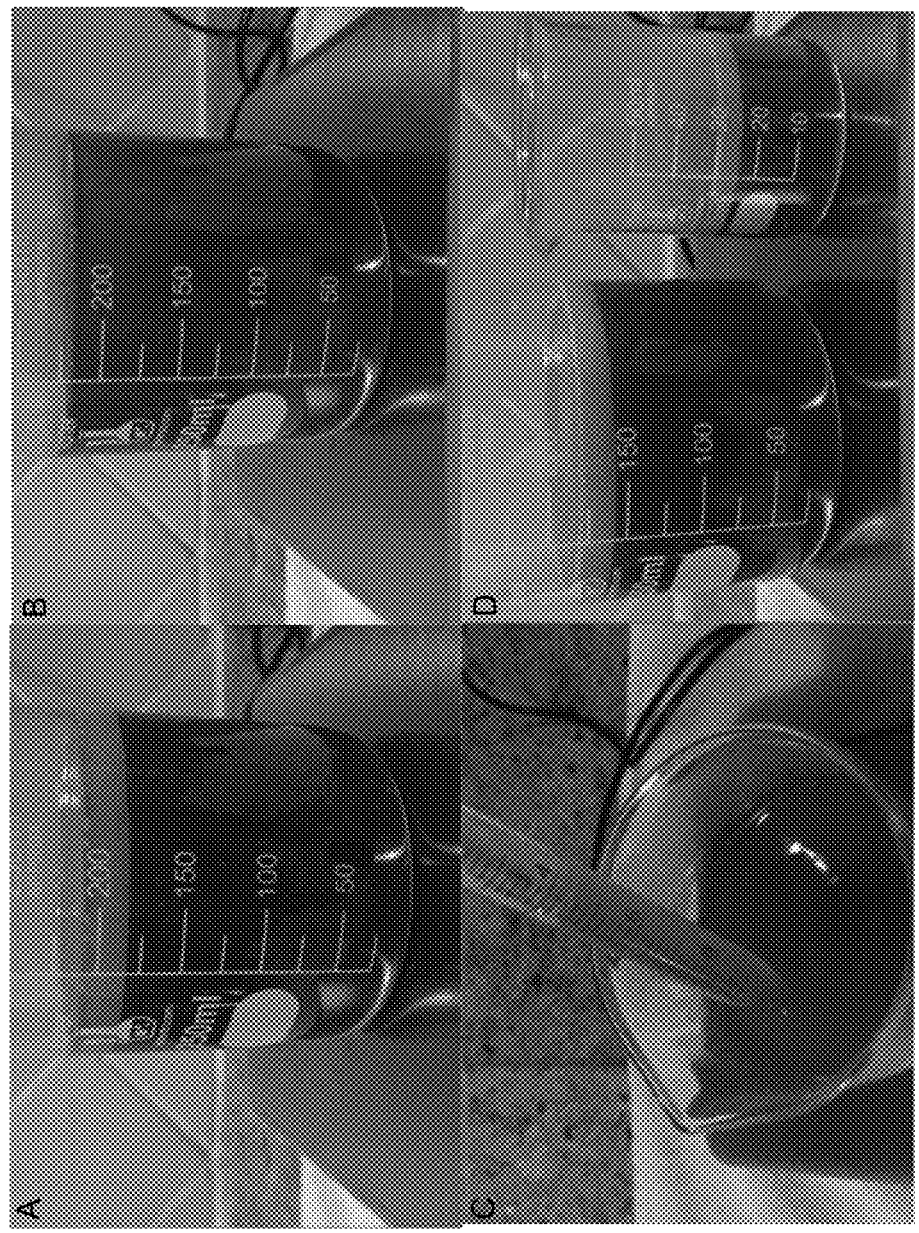
FIG. 12 shows homogenous emulsification where coffee having natural emulsifying properties was used.

Another example, wherein coffee having natural emulsifying properties was used. FIG. 12 shows full homogenous emulsification 1200 where 92.5% coffee and 7.5% oil mixture composed of lecithin and natural oils was homogenized without any additional emulsifying agents as shown in FIG. 12(B). Before homogenization, the solution appeared as FIG. 12A (note the separate layers). The product was extracted (as shown in FIG. 12C) in its maximum homogenized state to a destination container. The result is a product that maintains the volumetric proportions of oil and water in solution is shown in FIG. 12D. The extraction occurs while the solution is under mechanical action and at maximum homogenization. The dispensing apparatus can be those typically used in laboratory settings, such as the use of a pipette, nozzle, vacuum pump, or other extraction and/or dispensing routes, vehicles, or techniques to dispense in separate destination containers.

In one aspect, the composition is a homogenous stable oil-in-aqueous composition.

In one aspect, the homogenization is conducted in a temperature in the range of 20° C.-95° C.

In one aspect, the homogenization is conducted in a time-regulated manner.

In one aspect, the homogenization is carried out for at least one half second.

In one aspect, the maximum separation of oil from water occurs within three hours.

In one aspect, the homogenization is performed using colloid mills, rotor/stator homogenizers, high pressure homogenizers, sonicating homogenizers, mechanical shaking or stirring, centrifugal force or spinning, electrical, radio, and other types of energy to induce mixing of oil and aqueous phases.

As a general matter (with detailed examples below), to make a solution of the embodied compositions a holding vessel will be applied to an apparatus that allows continuous mixture. In some embodiments, the apparatus includes a magnetic stirring mechanism that mixes the solution with a magnetic stirrer inside a beaker (i.e. holding vessel). There is an extraction and dispensing apparatus to transfer the prepared solution to another vessel or destination bottle or packaging. A pipette, nozzle, or vacuum pump may be used to extract or dispense maximally homogenized product to a destination vessel.

With respect to the extraction process generally, the extraction is best conducted with the oil-water solution at its maximum or near maximum mixed (i.e., homogenized) state under continuous shaking, stirring, sonicating, spinning, agitation, or otherwise homogenization via movement, action, and/or mixing of molecules. The emulsified product is extracted fractionally to a designation container. The resulting extraction maintains the volumetric proportions of constituent compositions in the solution. An incorrect extraction and dispensing may cause uneven distribution of constituent compositions to destination containers, and result in an increase of oil or aqueous concentrations if not extracted under maximum or near maximum homogenized state.

EXAMPLES

Example 1: Molecular Fragrance/Deodorizer

This example provides a general procedure for the preparation of the emulsions of the present invention. The following procedures highlight the steps for preparing ten 10 mL bottles of a 33% total oil concentration molecular fragrance product. A 1.0% total concentration esterified polysorbate and/or polyalkylene emulsification agent(s), such as polyethylene glycol, is used to facilitate the mixture of oil and water. The remaining 66 mL consists of distilled water. The 33% oil composition utilizes coconut oil as a carrier and composed of 18 mL aromatic oil blend and 15 mL coconut oil carrier.

The composition of the preparation is as follows:

33 mL oil mixture,
66 mL water, and
1 mL PEG-200.

The materials above should be at room temperature. They were added and mixed at room temperature. Prepare a clean 150 mL or larger beaker and clean magnetic stirring rod. Add the stirring rod to the beaker. Add the water to a beaker sitting on a magnetic plate. The magnetic stirrer started to stir the water at this point. To the 66 mL of water add the 33 mL oil mixture. Alternatively, turn on the magnetic stirrer at this point and begin to stir the water and oil. The oil and water solution is in a continuous stirred state. To this state add the emulsification agent in a dropwise manner until 1 mL of polyethylene glycol has been added. The appearance of the solution should be homogeneous. With the solution in a continuous stirred state, extract and transfer the liquid in homogeneous form with a pipette to clean 10 mL bottles. The resulting solvent-free product is stable for over one year and should be kept in cool and dark conditions to protect against light and temperature.

Example 2—Non-Toxic Topical

The same general procedure of Example 1 was followed for the preparation of this emulsion. The purpose of this example is to demonstrate a preparation that contains no esterified materials that may damage or denature active ingredients. This preparation of ten 10 mL bottles of a 5.0% vitamin D topical preparation does not contain any esterified products. A total oil concentration of 33% is selected, and since vitamin D is an oil the total oil composition is as follows:

5 mL vitamin D oil
28 mL coconut oil carrier

Note that the remaining 28 mL of oil could be made with other compositions to contain additional properties including aromatic, therapeutic, and cleansing.

The composition of the preparation is as follows:

33 mL oil mixture,
34 mL ocean water, and
33 mL frankincense water.

The materials above should be at 30° C. They are to be added and mixed at 30° C. Note the complete absence of additional emulsifying agent(s). This was due in whole part by the emulsification properties of the ocean water and frankincense water. Other waters with emulsification properties, including saltwater preparations and other distilled waters, may have been used instead. The result of these natural emulsifying waters and/or oils are products that match the key features and characteristics of this invention defined elsewhere.

Prepare a clean 150 mL or larger beaker and clean magnetic stirring rod and hot plate. The hot plate was on a mild setting to maintain a temperature of 30° C. Add the stirring rod to the beaker. Add the 67 mL water mixture composed of ocean water and frankincense water to a beaker sitting on a magnetic plate. The magnetic stirrer may be started to stir the water at this point. To the 67 mL of water add the 33 mL oil mixture. The appearance of the solution should now be homogeneous. With the solution in a continuous stirred state, extract and transfer the liquid in homogeneous form with a pipette to clean 10 mL bottles. The resulting non-toxic product is stable for over one year and should be kept in cool and dark conditions to protect against light and temperature.

Example 3—Minimum Risk Pesticide/General Purpose Cleanser

The same general procedure of Example 2 was followed for the preparation of this emulsion. Preparing four 25 mL bottles of a 20% total oil concentration multipurpose molecular fragrance product. A 0.5% total concentration esterified polysorbate and/or polyalkylene emulsification agent(s), such as polysorbate, is used to facilitate the mixture of oil and water. Cedarwood essential oil is utilized in the oil composition for its pesticidal and aromatic qualities. The remaining 78.5 mL consists of ionized water. The ionized water contains its own emulsification properties. This example highlights that additional emulsifying agent(s) may be added to solution to augment homogenization persistence qualities. The 20% oil composition utilizes coconut oil as a carrier and composed of 15 mL cedarwood oil and 5 mL coconut oil carrier.

The composition of the preparation is as follows:
- 20 mL oil mixture,
- 78.5 mL ionized water, and
- 0.5 mL polysorbate 60.

The materials above should be at room temperature. They are to be added and mixed at room temperature. Prepare a clean 150 mL or larger beaker and clean magnetic stirring rod. Add the stirring rod to the beaker. Add the water to a beaker sitting on a magnetic plate. The magnetic stirrer may be started to stir the water at this point. To the water add the 20 mL oil mixture. Alternatively, turn on the magnetic stirrer at this point and begin to stir the water and oil. The oil and water solution should now be in a continuous stirred state. To this state add the emulsification agent in a dropwise manner until 0.5 mL of polysorbate has been added. The appearance of the solution should now be homogeneous. With the solution in a continuous stirred state, extract and transfer the liquid in homogeneous form with a pipette to clean 25 mL bottles. The resulting solvent-free product is stable for over one year and should be kept in cool and dark conditions to protect against light and temperature.

Example 4—Molecular Fragrance/Cleanser

The same general procedure of Example 3 is followed for the preparation of this emulsion. This example is for preparing four 25 mL bottles of a 20% total oil concentration multipurpose molecular fragrance product. A 0.5% total concentration esterified polysorbate and/or polyalkylene emulsification agent(s), such as polysorbate, is used to facilitate the mixture of oil and water. Cedarwood essential oil is utilized in the oil composition for its pesticidal and aromatic qualities. The remaining 78.5 mL consists of distilled water. This example highlights the ultra-low concentration of emulsifier needed in the absence of other emulsification agents. The low concentration of emulsifier is necessary to achieve the desired characteristics and outcomes of the present invention as outlined above. The 20% oil composition utilizes coconut oil as a carrier and composed of 15 mL cedarwood oil and 5 mL coconut oil carrier.

The composition of the preparation is as follows:
- 20 mL oil mixture,
- 78.5 mL distilled water, and
- 0.5 mL polysorbate 60.

The materials above should be at 25-27° C. They are to be added and mixed at 25-27° C. Prepare a clean 150 mL or larger beaker and clean magnetic stirring rod. Add the stirring rod to the beaker. Add the water to a beaker sitting on a magnetic and hot plate. The hot plate should be set to a mild setting to maintain a temperature of 27° C. The magnetic stirrer may be started to stir the water at this point. To the water add the 20 mL oil mixture. Alternatively, turn on the magnetic stirrer at this point and begin to stir the water and oil. The oil and water solution should now be in a continuous stirred state. To this state add the emulsification agent in a dropwise manner until 0.5 mL of polysorbate has been added. The appearance of the solution should now be homogeneous. With the solution in a continuous stirred state, extract and transfer the liquid in homogeneous form with a pipette to clean 25 mL bottles. The resulting solvent-free product is stable for over one year and should be kept in cool and dark conditions to protect against light and temperature.

Example 5—Fragranced Probiotic Topical

The same general procedure of Example 3 is followed for the preparation of this emulsion. This example is for preparing 100 mL of 25% total oil in water topical probiotic product. This example highlights the addition of *lactobacillus* for a functional benefit. The formulation outlined here is inspired by FDA monographs for the treatment of bacterial vaginosis. This formula highlights the emulsification properties of biologics wherein freeze-dried bacteria are utilized in its preparation and contribute to the emulsification of the product. This formula consists of a complete emulsion by saltwater. A 26.3% saline solution is prepared by dissolving 357 grams of salt in one liter of water at 20° C. The 25% oil composition consists of 15 mL cedarwood oil and 10 mL coconut oil carrier. Additional oils including vitamin oils may also be added. The freeze-dried *L. helveticus* Rosell®-52 (R0052) is available for procurement by specialized distributors, and is available at a concentration of $50 \times 10^9$ CFU/gm.

The composition of the preparation is as follows:
- 25 mL oil mixture,
- 75 mL 26.3% saline, and
- 25 gm ($1.25 \times 10^{12}$ CFU) *L. helveticus* Rosell®-52 (R0052) freeze-dried powder.

The water and oil should be available at room temperature, and mildly heated to 27° C. Prepare a clean 150 mL or larger beaker and clean magnetic stirring rod. Add the stirring rod to the beaker. Add the water to a beaker sitting on a magnetic and hot plate. The hot plate should be at a setting to maintain a temperature of 27° C. The magnetic stirrer may be started to stir the water at this point. To the water add the 25 mL oil mixture. Alternatively, turn on the magnetic stirrer at this point and begin to stir the water and oil. The oil and water solution should now be in a continuous stirred state. The appearance of the solution should now be homogeneous. Slowly add the 25 grams of probiotics, and slowly increase the temperature up to 30° C. as needed to dissolve the powder. The freeze-dried bacteria will not be reconstituted in this formula since there is no agar or broth. Furthermore, the presence of pesticidal and/or anti-microbial cedarwood oil also prohibits the reconstitution and subsequent replication of the freeze-dried bacteria. With the solution in a continuous stirred state, extract and transfer the liquid in homogeneous form with a pipette to clean bottles. The resulting solvent-free product is stable for over one year and should be kept in cool and dark conditions to protect against light and temperature.

Example 6—Aqueous Emulsion

This example provides a general procedure for the preparation of the emulsions and nanoemulsions made without any additional emulsifying agent. The result produces 100 10 mL bottles of a 33% total oil concentration molecular topical product. Coffee is the primary emulsifying agent in this example. Coffee itself is a solution composed of many types of molecules that provide an innate ability to emulsify oil and water to a full and partial mixed state. This formula requires 670 mL brewed coffee to be prepared separately. The 33% oil mixture is composed of 180 mL aromatic essential oil blend and 150 mL vitamin E oil.

The composition of the preparation is as follows:
- 330 mL oil mixture, and
- 670 mL brewed coffee.

Prepare a clean 1500 mL or larger beaker and clean magnetic stirring rod. Add the stirring rod to the beaker. Add the coffee to a beaker sitting on a magnetic plate. The magnetic stirrer may be started to stir the coffee at this point. To the 670 mL of coffee add the 330 mL oil mixture. Alternatively, turn on the magnetic stirrer at this point and begin to stir the coffee and oil. The oil and coffee solution should now be in a continuous stirred state. The coffee and oil will now be in a state of emulsion. With the solution in a continuous stirred state, extract and transfer the liquid in homogeneous form with a pipette to clean 10 mL bottles. The resulting solvent-free product is stable for over one year and should be kept in cool and dark conditions to protect against light and temperature.

Example 7—Ocean Water Fragrance

This example provides a general procedure for the preparation of the emulsions and nanoemulsions made with trace amounts of emulsifying agent. The result produces 100 10 mL bottles of a 33% total oil concentration molecular fragrance product. Ocean water is the primary emulsifying agent in this example. Ocean water itself is a solution whose composition contains emulsifying properties with ability to mix oil and water fully, and partially when diluted with non-emulsifying water. This formula adds 0.5% polysorbate emulsifying agent to persist the homogenized state of products for a greater period of time. The remainder of the 33% oil mixture is composed of 220 mL aromatic essential oil blend and 60 mL unscented coconut oil carrier.
The composition of the preparation is as follows:
  280 mL oil mixture,
  50 mL polysorbate, and
  670 mL ocean water.
Prepare a clean 1500 mL or larger beaker and clean magnetic stirring rod. Add the stirring rod to the beaker. Add the ocean water to a beaker sitting on a magnetic plate. The magnetic stirrer may be started to stir the ocean water at this point. To the 670 mL of ocean water add the 330 mL oil mixture. Alternatively, turn on the magnetic stirrer at this point and begin to stir the ocean water and oil. The oil and ocean water solution should now be in a continuous stirred state. The ocean water and oil will now be in a state of emulsion. With the solution in a continuous stirred state, extract and transfer the liquid in homogeneous form with a pipette to clean 10 mL bottles. The resulting solvent-free product is stable for over one year and should be kept in cool and dark conditions to protect against light and temperature.

Example 8—Naturally Emulsifying Oil

This example provides a general procedure for the preparation of the emulsions and nanoemulsions made without any additional emulsifying agent. The result produces 100 10 mL bottles of a 33% total oil concentration molecular topical product. Tocopherol (vitamin E) is the primary emulsifying agent in this example. It is an oil soluble molecule with an innate ability to emulsify oil and water to a full and partial mixed state. This formula mixes the oil solution with 670 mL water. The 33% oil mixture is composed of 180 mL aromatic essential oil blend and 150 mL vitamin E oil.
The composition of the preparation is as follows:
  330 mL oil mixture, and
  670 mL water.
Prepare a clean 1500 mL or larger beaker and clean magnetic stirring rod. Add the stirring rod to the beaker. Add the water to a beaker sitting on a magnetic plate. The magnetic stirrer may be started to stir the water at this point. To the 670 mL of water add the 330 mL oil mixture. Alternatively, turn on the magnetic stirrer at this point and begin to stir the water and oil. The oil and water solution should now be in a continuous stirred state. The water and oil will now be in a state of emulsion. With the solution in a continuous stirred state, extract and transfer the liquid in homogeneous form with a pipette to clean 10 mL bottles. The resulting solvent-free product is stable for over one year and should be kept in cool and dark conditions to protect against light and temperature.

It should be noted that the above-mentioned examples having methods listed as volumes of particular constituent liquids are not limited to those particular volumes, but can be accomplished with other volumes, but retaining approximate percentages of constituent compositions.

While the foregoing describes various embodiments of the invention, other and further embodiments of the invention may be devised without departing from the basic scope thereof. The scope of the invention is determined by the claims that follow.

The invention is not limited to the described embodiments, versions, or examples, which are included to enable a person having ordinary skill in the art to make and use the invention when combined with information and knowledge available to the person having ordinary skill in the art.

The foregoing description of embodiments is provided to enable any person skilled in the art to make and use the subject matter. Various modifications to these embodiments will be readily apparent to those skilled in the art, and the novel principles and subject matter disclosed herein may be applied to other embodiments without the use of the innovative faculty. The claimed subject matter outlined in the claims is not intended to be limited to the embodiments shown herein but is to be accorded to the widest scope consistent with the principles and novel features disclosed herein. It is contemplated that additional embodiments are within the spirit and true scope of the disclosed subject matter.

I claim:
1. A composition comprising
   a) at least one oil phase;
   b) at least one aqueous phase;
   c) at least one emulsifier, wherein the at least one emulsifier is any or combination of at least one emulsifier agent, water with emulsification properties, oil with emulsification properties, and active ingredient with emulsification properties; and
   d) optionally, one or more biologically active ingredients;
      wherein the at least one oil phase is an aromatic essential oil having natural anti-pesticidal and anti-inflammatory properties and is between 5% and 50% of a total weight of the composition;
      wherein the at least one aqueous phase is comprised of a distilled water product derived from of at least one of rose water, peppermint, frankincense, cumin, and orange blossom water, and wherein the at least one aqueous phase is between 50% to 95% total weight of the composition;
      wherein the at least one emulsifier includes at least one of polysorbate and polyethylene glycol (PEG), and wherein the at least one emulsifier is between 0% and 5% of the total weight of the composition; and
      wherein the one or more biologically active ingredient is comprised of a biochemical macromolecule that includes at least one of vitamins, antioxidants, polyphenols, terpenoids, flavonoids, carotenoids, cannabinoids, alpha-hydroxy acids, beta-hydroxy acids, organic peroxides, and amino acids, and wherein the one or more biologically active ingredients is between 0% and 50% of the total weight of the composition.

* * * * *